US010463804B2

(12) United States Patent
Montgomery et al.

(10) Patent No.: US 10,463,804 B2
(45) Date of Patent: Nov. 5, 2019

(54) MEDICAMENT DEVICE FOR USE WITH A CONVENTIONAL SYRINGE

(71) Applicants: Steven M. Montgomery, Los Angeles, CA (US); Gregory E. Mote, Big Bear Lake, CA (US)

(72) Inventors: Steven M. Montgomery, Los Angeles, CA (US); Gregory E. Mote, Big Bear Lake, CA (US)

( * ) Notice: Subject to any disclaimer, the term of this patent is extended or adjusted under 35 U.S.C. 154(b) by 145 days.

(21) Appl. No.: 15/707,111

(22) Filed: Sep. 18, 2017

(65) Prior Publication Data

US 2018/0078712 A1   Mar. 22, 2018

Related U.S. Application Data

(60) Provisional application No. 62/398,515, filed on Sep. 22, 2016, provisional application No. 62/507,077, filed on May 16, 2017.

(51) Int. Cl.
*A61M 5/32* (2006.01)
*A61M 5/00* (2006.01)
(Continued)

(52) U.S. Cl.
CPC .......... *A61M 5/3202* (2013.01); *A61M 5/002* (2013.01); *A61M 5/31571* (2013.01);
(Continued)

(58) Field of Classification Search
CPC ........ A61M 5/3202; A61M 2005/2013; A61M 2005/208; A61M 2005/2073; A61M 2005/3267; A61M 5/3271; A61M 5/3272; A61M 5/2033; A61M 5/002; A61M 5/31571; A61M 5/31585; A61M 5/3257; A61M 2005/3254; A61M 2005/328
See application file for complete search history.

(56) References Cited

U.S. PATENT DOCUMENTS 5,681,291 A   10/1997 Galli
6,767,336 B1   7/2004 Kaplan
(Continued)

FOREIGN PATENT DOCUMENTS

EP   2399627   12/2011

OTHER PUBLICATIONS owenmumford.com, May 15, 2018, Internet printout: https://www.owenmumford.com/us/healthcare-professionals-product/autoject-2/.
(Continued)

*Primary Examiner* — Bhisma Mehta
*Assistant Examiner* — Nidah M Hussain
(74) *Attorney, Agent, or Firm* — Todd R. Miller

(57) ABSTRACT

The novel devices comprise a housing that preferably contains a preloaded, conventional syringe with medication. Both trained and untrained users may administer an injection safely and conveniently to themselves or others in myriad settings. The disclosed devices rely on the user's manual action to insert the needle. Only after the needle is fully inserted is the medicament delivered, resulting in a safer injection. After use, the devices include a locking mechanism that locks a spring-loaded sheath in place around the needle for protection. As a common syringe is utilized, engineering and production issues of automatic injectors' custom syringe assemblies are avoided.

8 Claims, 21 Drawing Sheets

(51) Int. Cl.
*A61M 5/315* (2006.01)
*A61M 5/20* (2006.01)

(52) U.S. Cl.
CPC ...... *A61M 5/31585* (2013.01); *A61M 5/3257* (2013.01); *A61M 2005/2073* (2013.01); *A61M 2005/328* (2013.01); *A61M 2005/3254* (2013.01); *A61M 2005/3267* (2013.01)

(56) References Cited

U.S. PATENT DOCUMENTS

2018/0015226 A1    1/2018   Cowe
2018/0015233 A1*   1/2018   Takemoto ............... A61M 5/32

OTHER PUBLICATIONS

West Pharmaceutical Services, Inc., SelfDose Information Sheet, Copyright 2017.

* cited by examiner

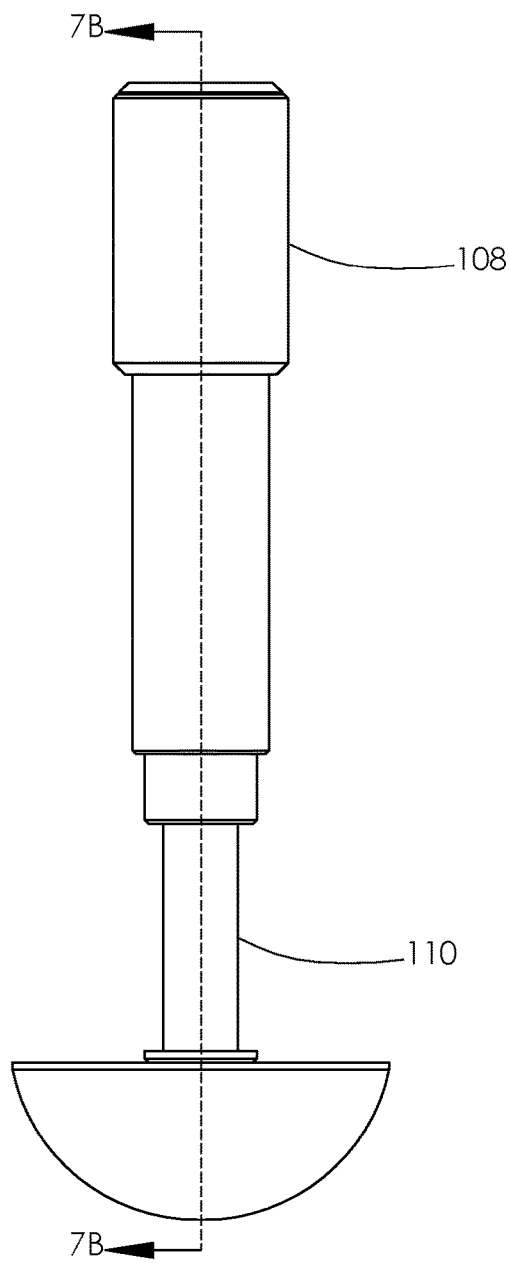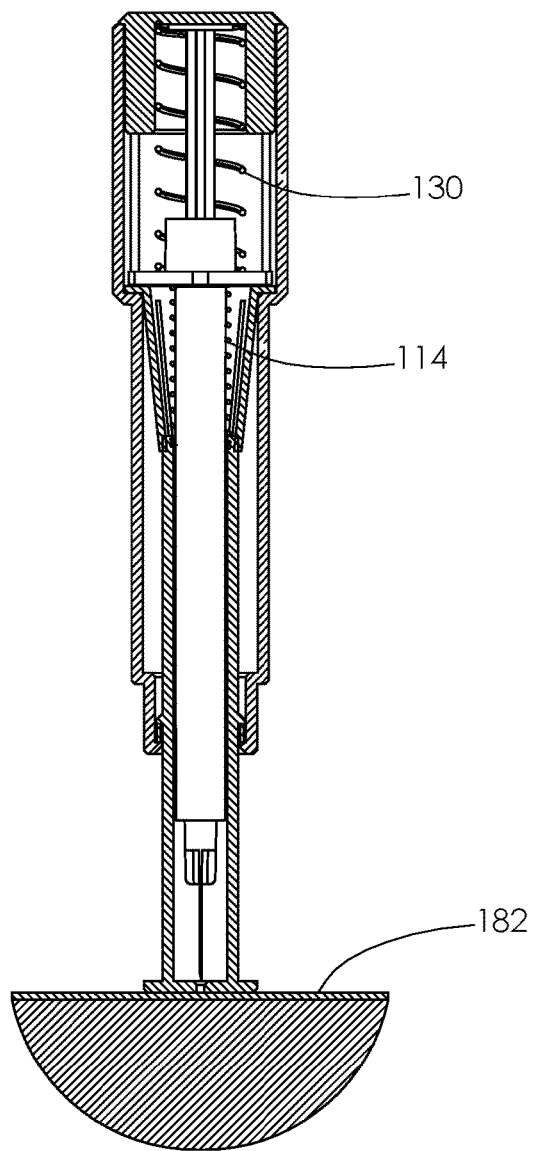
Fig. 7A
Fig. 7B

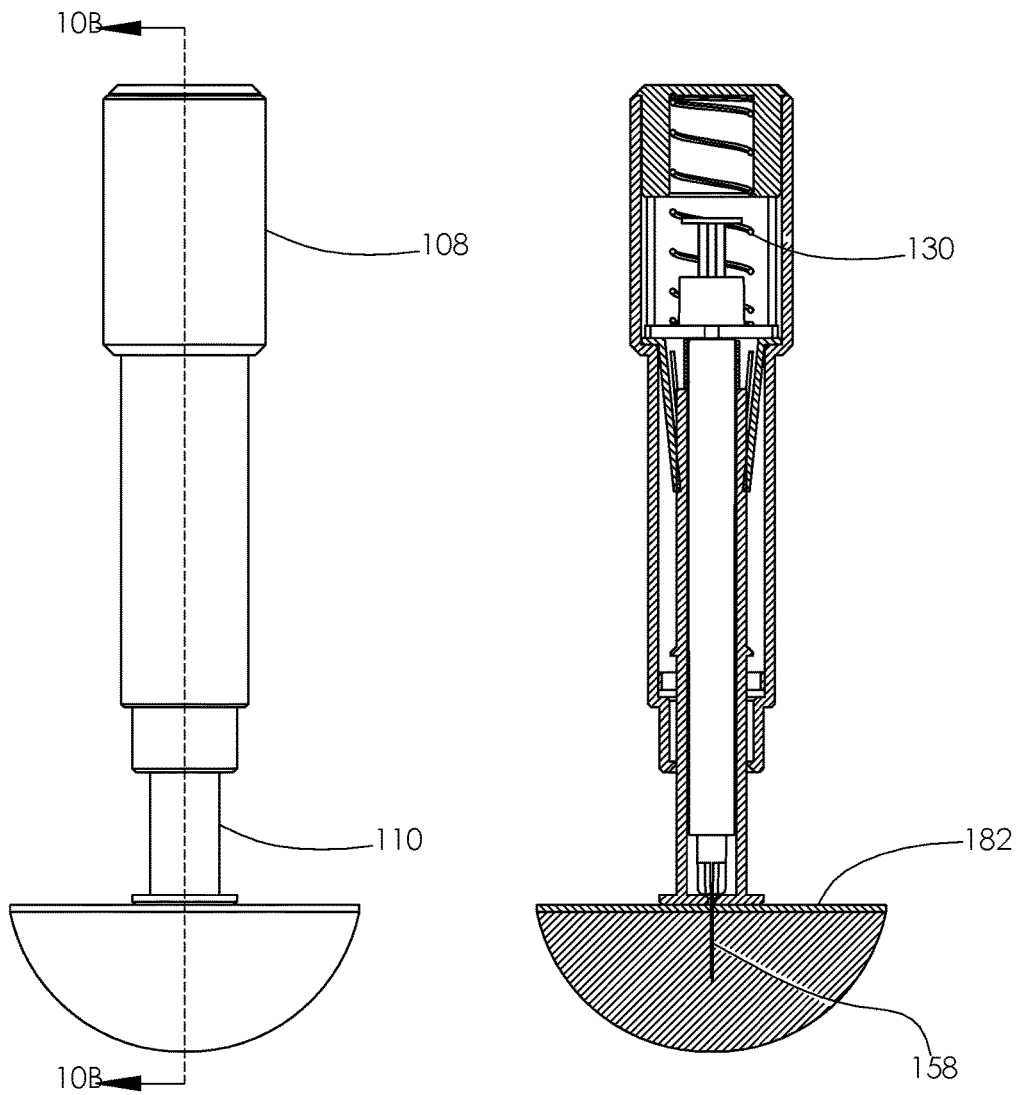

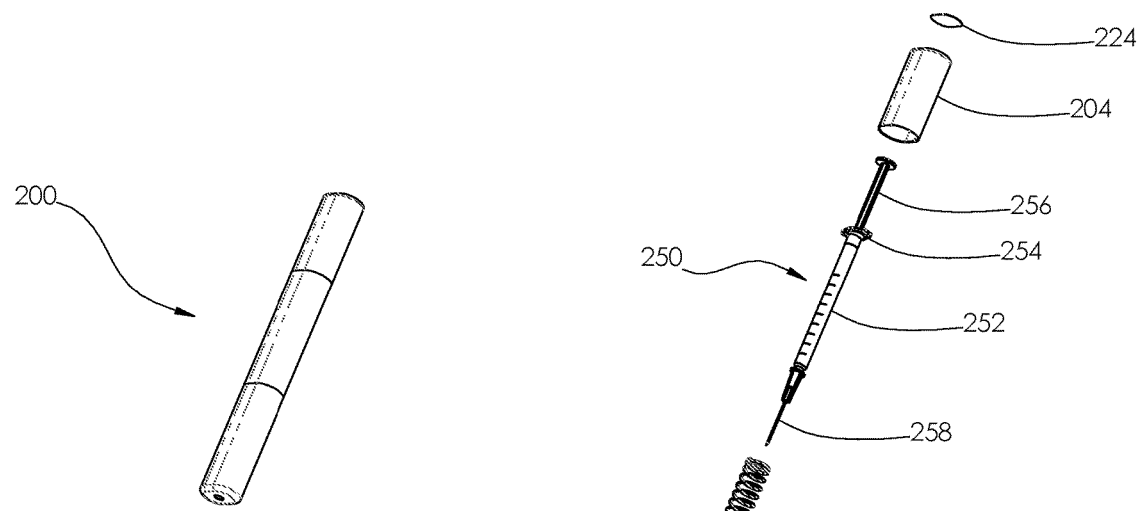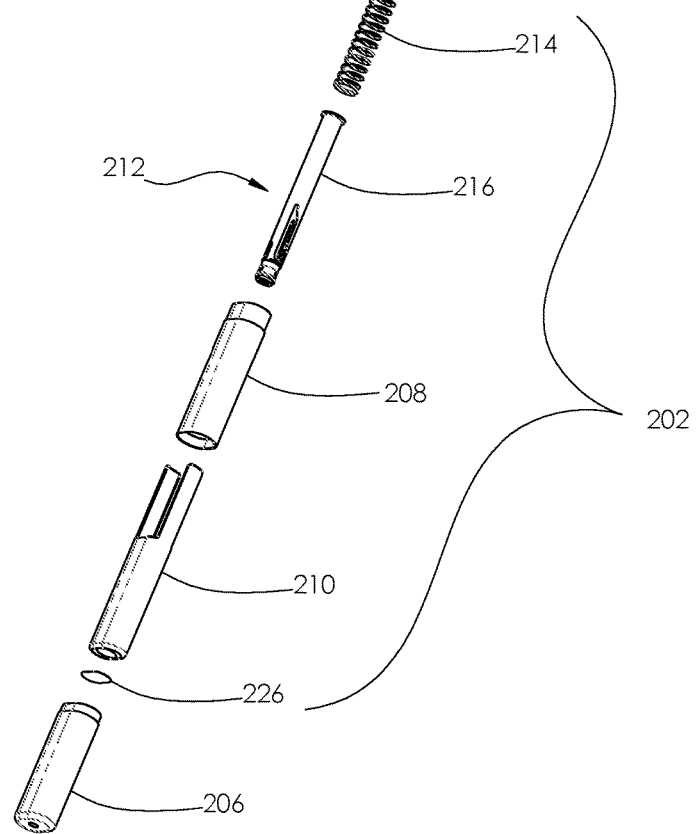
Fig. 14A
Fig. 14B

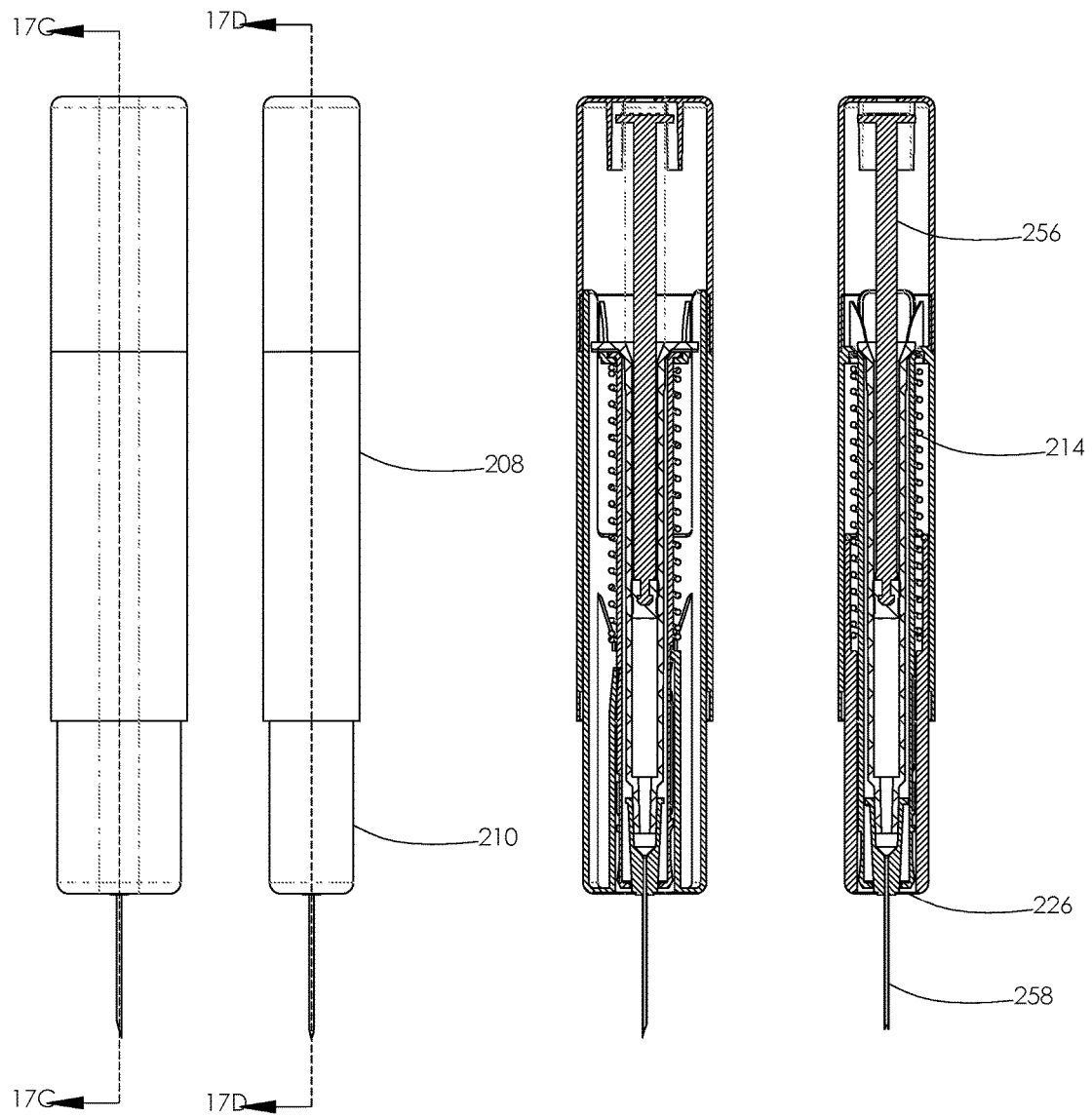

MEDICAMENT DEVICE FOR USE WITH A CONVENTIONAL SYRINGE

CROSS-REFERENCE TO RELATED APPLICATIONS

The present application claims benefit of and priority to U.S. Provisional Patent Application Ser. No. 62/398,515 filed on Sep. 22, 2016, as well as U.S. Provisional Patent Application Ser. No. 62/507,077 filed on May 16, 2017. Each application is incorporated by reference as if fully set forth herein.

BACKGROUND

The present disclosure relates generally to a device for injecting or otherwise administrating a medication.

SUMMARY

One exemplary embodiment of the disclosed subject matter is a hand-held device comprising a body assembly preferably configured to receive a conventional syringe. The body assembly has a top and an opposing bottom. A housing cap is disposed at the top of the body assembly. A first spring is disposed between the body assembly and housing cap. The body assembly may comprise a housing, a sheath slideably contained within the housing, a sheath lock disposed within the housing opposite the sheath, and a second spring disposed within the sheath lock.

The medicament device may further comprise a sheath clip disposed in an annular groove within the housing for retaining the sheath during handling of the device. The device may also include a sheath cap disposed about the bottom of the body assembly. The sheath lock is preferably configured to frictionally engage flanges of a barrel of a conventional syringe. The housing and sheath are each preferably substantially the same length as the syringe barrel. The second spring preferably requires less compression force than the first spring.

Another exemplary embodiment of the disclosed subject matter is a device for administering medicament using a conventional syringe, wherein the device comprises a body assembly configured to receive the syringe. The body assembly has a top and an opposing bottom. A housing cap is disposed at the top of the body assembly. The body assembly preferably comprises a housing, a sheath slideably contained within the housing, a locking mechanism, and a sheath spring.

The locking mechanism may comprise a sleeve, sleeve tracks, and one or more sheath pins, wherein the sleeve is slideably disposed within the housing at an end opposite the sheath, wherein the sheath pins protrude from the interior of the sheath, and wherein the sleeve tracks are cut within the sleeve and configured to engage the one or more sheath pins. The sleeve tracks may be bifurcated to lock the sheath in place around a needle of the syringe after use of the device to administer medicament. The locking mechanism may further comprise sheath snaps extending from the interior of the sheath, wherein the sheath snaps may be engaged by sheath fingers extending from one end of the sheath.

In the alternative, the locking mechanism may comprise a sheath lock disposed within the housing at an end opposite the sheath. The sheath lock is preferably configured to frictionally engage flanges of the syringe barrel. The device of this arrangement may further comprise a plunger spring disposed between the housing cap and the housing, wherein the plunger spring requires more compression force than the sheath spring.

Yet another exemplary embodiment of the disclosed subject matter is a method of using a device for administering medicament using a conventional syringe having a needle. The method may comprise utilizing a primary stroke to slide a sheath into a housing body containing the syringe and thereby expose the needle, wherein the primary stroke must overcome the force of a sheath spring biasing the sheath away from the housing body. The method may further comprise utilizing a secondary stroke to administer medicament contained within the syringe after the primary stroke is complete. After the secondary stroke is complete, a locking mechanism of the device may preclude the use of another primary stroke.

BRIEF DESCRIPTION OF THE DRAWINGS

Some non-limiting exemplary embodiments of the disclosed subject matter are illustrated in the following drawings. Identical or duplicate or equivalent or similar structures, elements, or parts that appear in one or more drawings are generally labeled with the same reference numeral, optionally with an additional letter or letters to distinguish between similar objects or variants of objects, and may not be repeatedly labeled and/or described. Dimensions of components and features shown in the figures are chosen for convenience or clarity of presentation. For convenience or clarity, some elements or structures are not shown or shown only partially and/or with different perspective or from different point of views.

FIG. 7A is a front view of the medicament device seen in FIG. 1, wherein the sheath is touching the skin of the site to be injected;

FIG. 7B is a sectional view of the medicament device and site taken along line 7B-7B seen in FIG. 7A;

FIG. 10A is a front view of the medicament device seen in FIG. 1, wherein the device is in a partially released state after the medicament contained in the syringe has been injected into the site;

FIG. 10B is a sectional view of the medicament device and site taken along line 10B-10B seen in FIG. 10A;

FIG. 14A is a perspective view of the medicament device seen in FIG. 13;

FIG. 14B is a fully exploded view of the medicament device seen in FIG. 13;

FIG. 17A is a front view of the medicament device seen in FIG. 16A with the needle deployed;

FIG. 17B is a side view of the medicament device seen in FIG. 16A with the needle deployed;

FIG. 17C is a sectional view of the medicament device taken along line 17C-17C seen in FIG. 17A;

FIG. 17D is a sectional view of the medicament device taken along line 17D-17D seen in FIG. 17B;

DETAILED DESCRIPTION

Figure 1:
FIG. 1 illustrates an embodiment of a medicament device disclosed herein in use.
Figure 2:
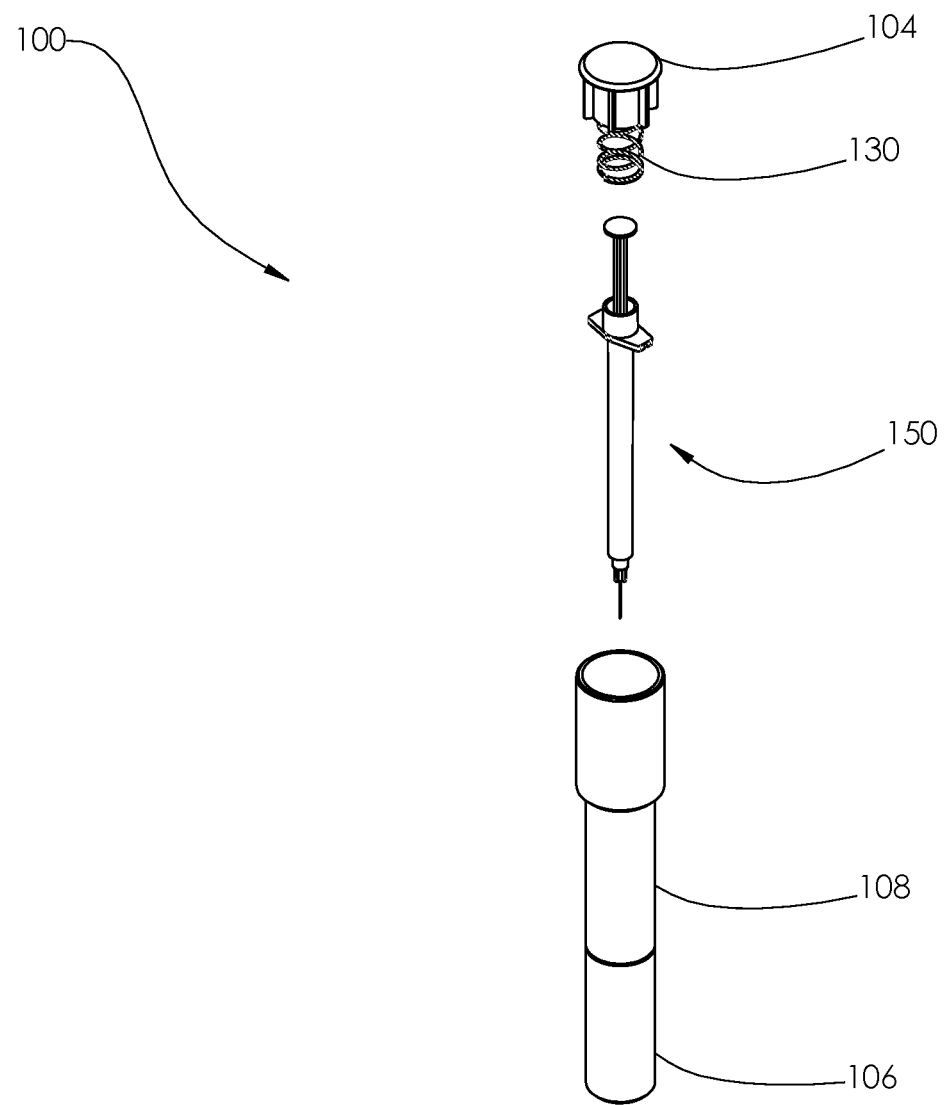
FIG. 2 is a partially exploded view of the medicament device seen in FIG. 1 with sheath cap attached at the bottom end of the device.

For safety and accuracy, injection by syringe requires skilled technique with formal training. Steps include uncapping the needle, piercing the membrane and drawing medicament from a vial, aligning the plunger tip with respective indices to measure a required dose, correctly inserting the needle into a proper injection site, squeezing the syringe plunger while keeping the syringe stable, and recapping the bio-hazardous needle. Issues with injection by syringe include aspiring incorrect dosage, lack of safe portability, tricky syringe manipulation in administering shot, accidental needle sticks, and unsuitable syringe disposal.

Related devices that automate injection include what is commonly referred to as an auto-injector. A conventional auto-injector contains a custom, spring-loaded and pre-filled syringe, which, when triggered by pressured contact, releases a spring-loaded needle into the injection site, squirting in the dose of medicament. Issues with auto-injectors include confusing labeling, unlocking of any safety mechanism, determining where on the device the needle will exit, and accidentally firing the device into a finger by touching the actuator tip.

Accordingly, a medicament device solving these and other problems is desired.

FIGS. 1-12B illustrate an embodiment of a device 100 for administering medicament using a conventional pre-filled syringe 150 such as 1 ml Becton Dickinson tuberculin syringe filled with epinephrine. Syringe 150 may comprise barrel 152, plunger 156 that slides within barrel 152, and needle 158. The barrel 152 typically has flanges 154 at one end that aid in pushing the plunger 156 through the barrel 152 containing medicament (not shown). Depending on the intended use of device 100, the medicament may be injected into a site 180 such as a deltoid, triceps, quadriceps or the like of a user or patient.

Medicament device 100 preferably comprises a body assembly 102, a sheath cap 108 at one end of the assembly 102, and a plunger spring 130 and housing cap 104 at the other end of the assembly 102.

Body assembly 102 may be comprised of a housing 108 containing sheath 110, locking mechanism 112, sheath clip 118, and sheath spring 114. The locking mechanism 112 preferably comprises a sheath lock 116. The sheath clip 118 disposed in an annular groove within housing 108. The sheath clip 118 retains the needle sheath 110 during handling of the device 100 until needle 158 insertion.

Figures 3A, 3B:
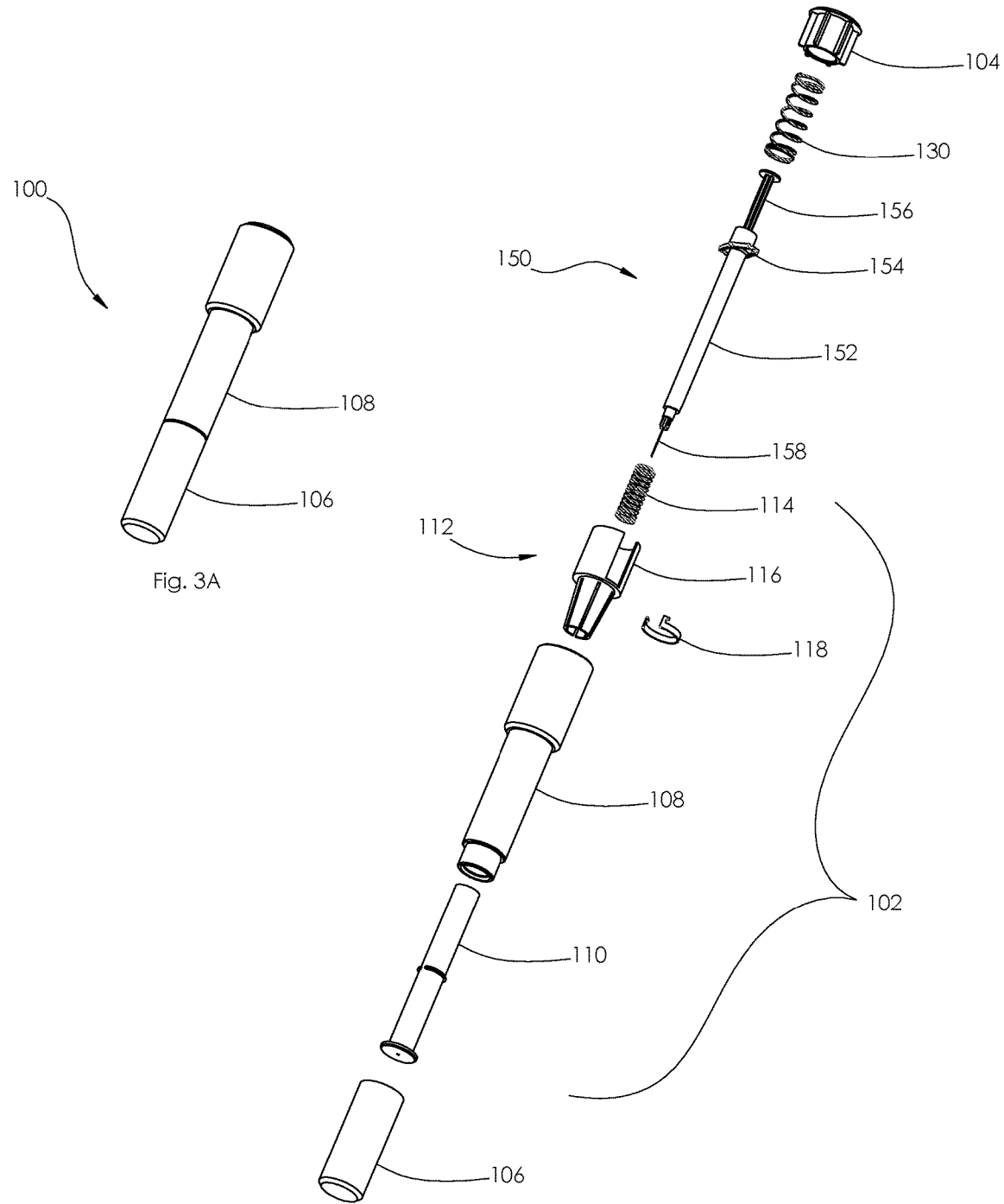
FIG. 3A is a perspective view of the medicament device seen in FIG. 2.
FIG. 3B is a fully exploded view of the medicament device seen in FIG. 2.

As best seen in FIG. 3B, housing 108 is generally tubular in shape with a top and an opposing bottom. The housing 108 may have a generally wider opening at the top compared to the bottom to be able to receive a conventional syringe 150 placed into the housing 108 from the top. The overall length of the housing 108 is about the same length of barrel 152 of syringe 150 158. Similarly, the overall length of sheath 110 is also about the same length of barrel 152 of syringe 150.

The top of housing 108 is also configured to receive the sheath lock 116. The sheath lock 116 itself has an opening at one end with a slot therein configured to receive and frictionally engage the flanges 154 of syringe 150.

The bottom of the housing 108 is configured to receive the sheath 110 wherein the sheath 110 may freely slide within the housing 108. Sheath lock 116 is not permitted to slide within housing 108 but instead is held firmly in place within housing 108.

When assembled, the entire syringe 150 with its needle 158 is encased within the device 100. Sheath cap 106 and sheath 110 surround the needle 158 when the device 100 is not in use. Housing cap 104 seals the top of the housing 108, wherein one end of plunger spring 130 abuts cap 104 while the other end of spring 130 abuts the flanges 154 of the syringe 150.

Figure 4A:
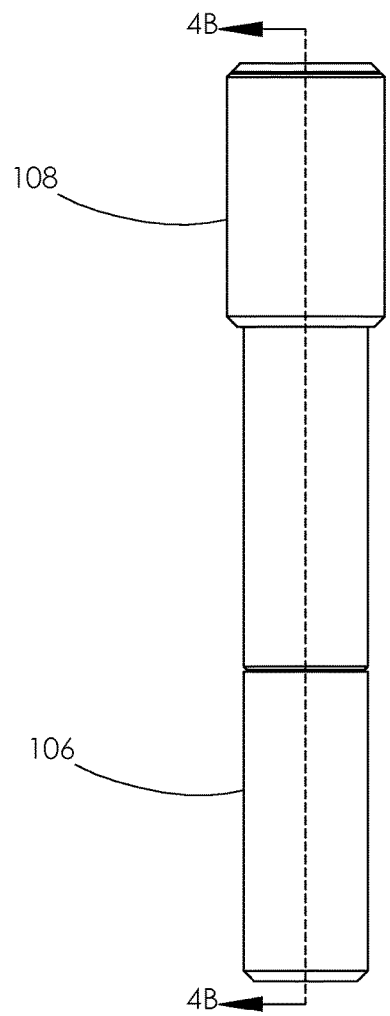
FIG. 4A is a front view of the medicament device seen in FIG. 2.
Figure 4B:
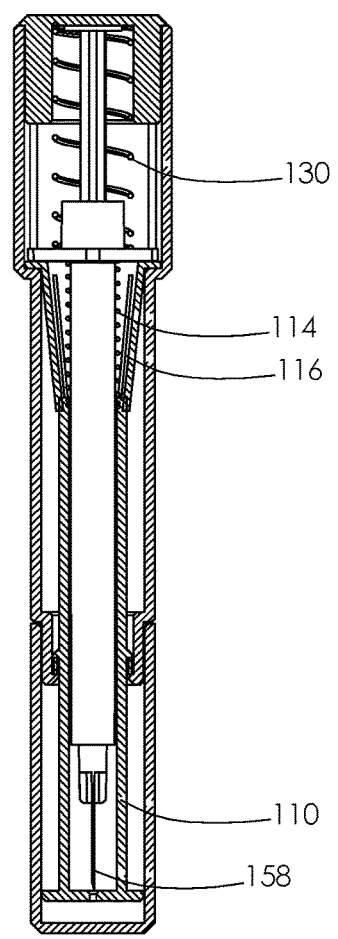
FIG. 4B is a sectional view of the medicament device taken along line 4B-4B seen in FIG. 4A.
Figures 5A, 5B:
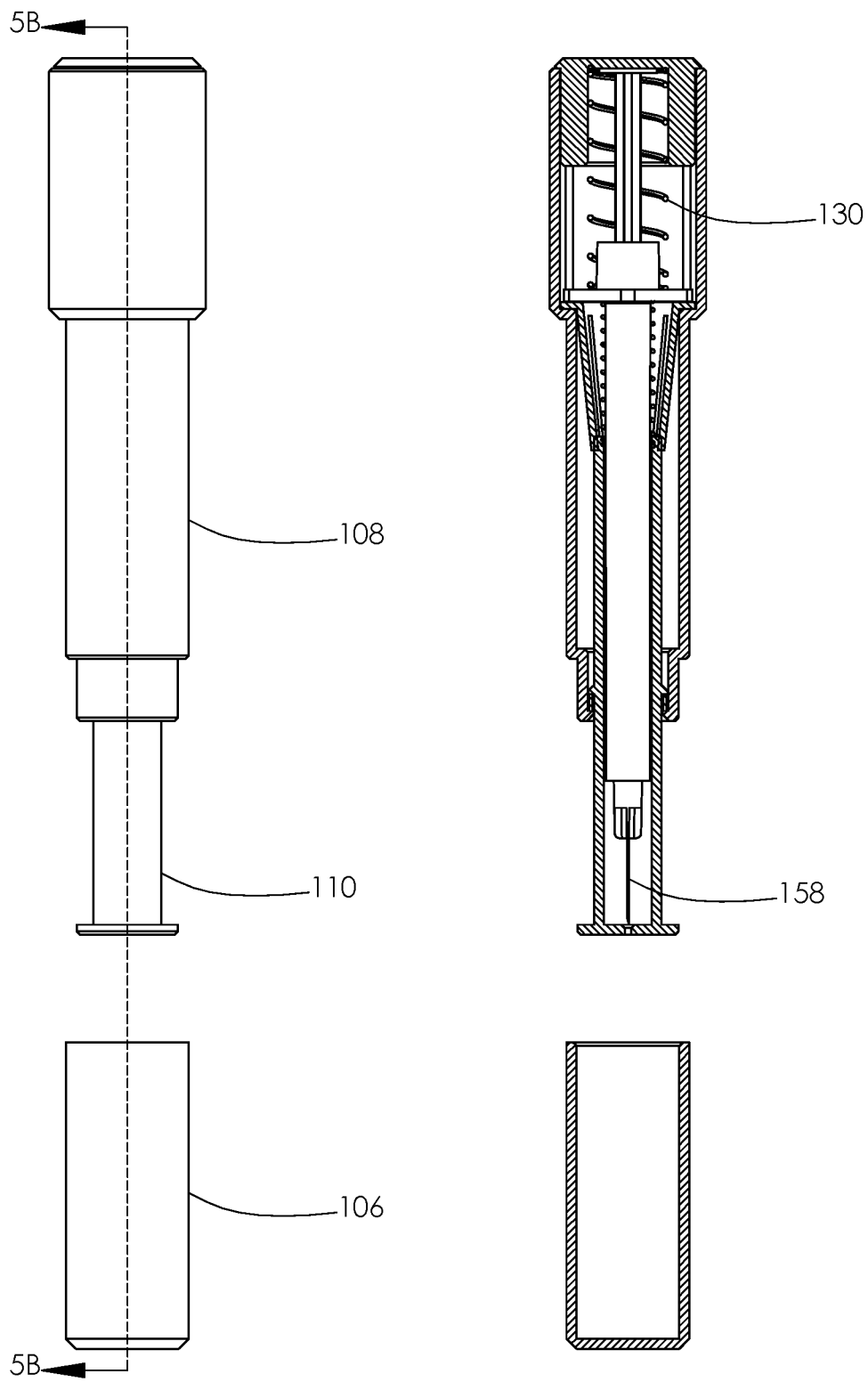
FIG. 5A is a front view of the medicament device seen in FIG. 2 with the sheath cap removed.
FIG. 5B is a sectional view of the medicament device taken along line 5B-5B seen in FIG. 5A.
Figures 6A, 6B:
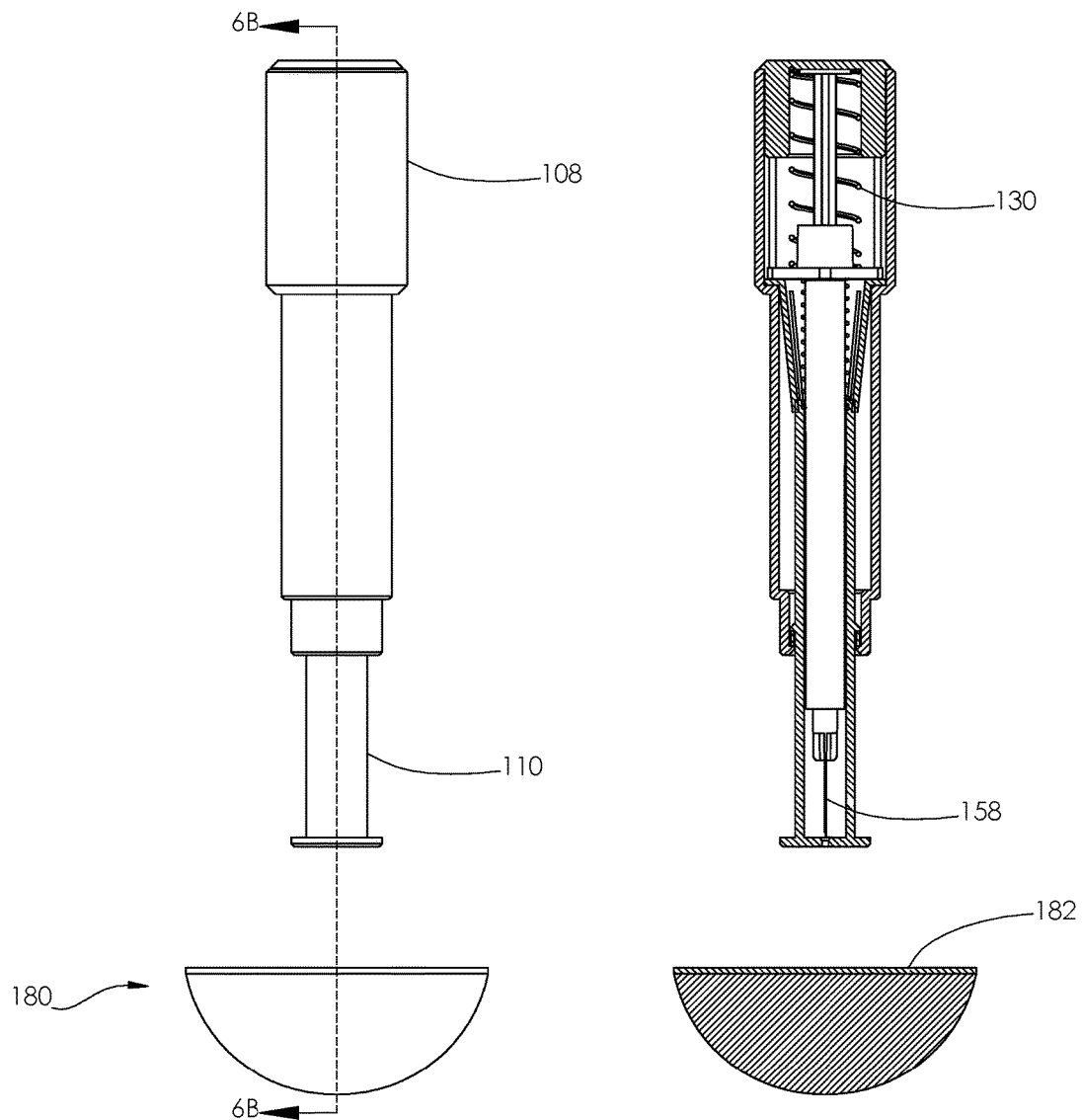
FIG. 6A is a front view of the medicament device seen in FIG. 1 disposed above the site to be injected.
FIG. 6B is a sectional view of the medicament device and site taken along line 6B-6B seen in FIG. 6A.
Figure 8A:
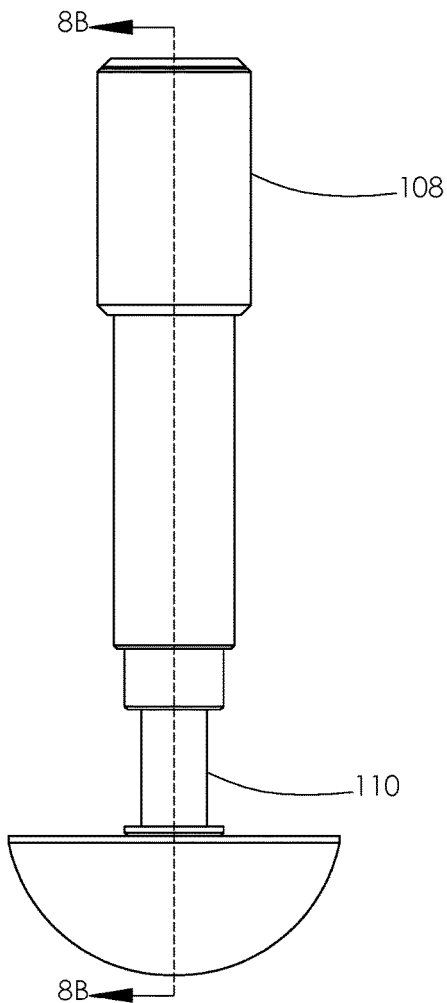
FIG. 8A is a front view of the medicament device seen in FIG. 1, wherein the needle of the syringe has been inserted into the skin.
Figure 8B:
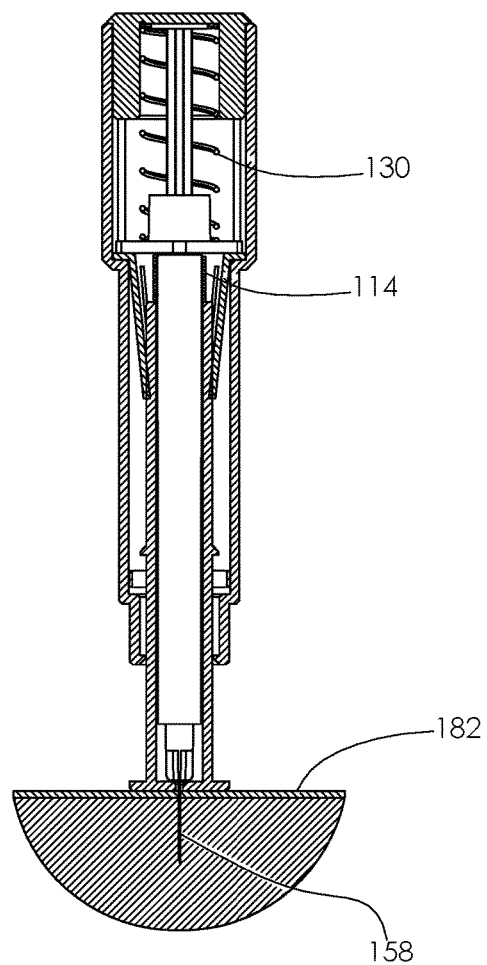
FIG. 8B is a sectional view of the medicament device and site taken along line 8B-8B seen in FIG. 8A.
Figure 9A:
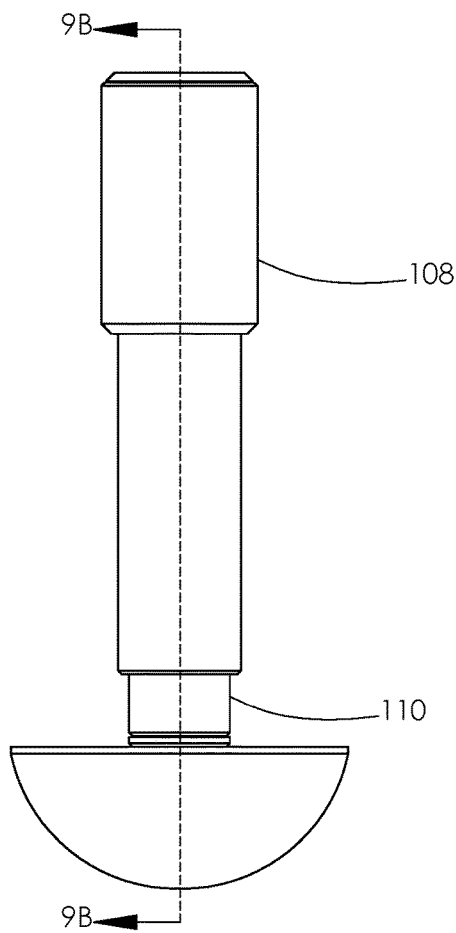
FIG. 9A is a front view of the medicament device seen in FIG. 1, wherein medicament contained in the syringe is injected into the site.
Figure 9B:
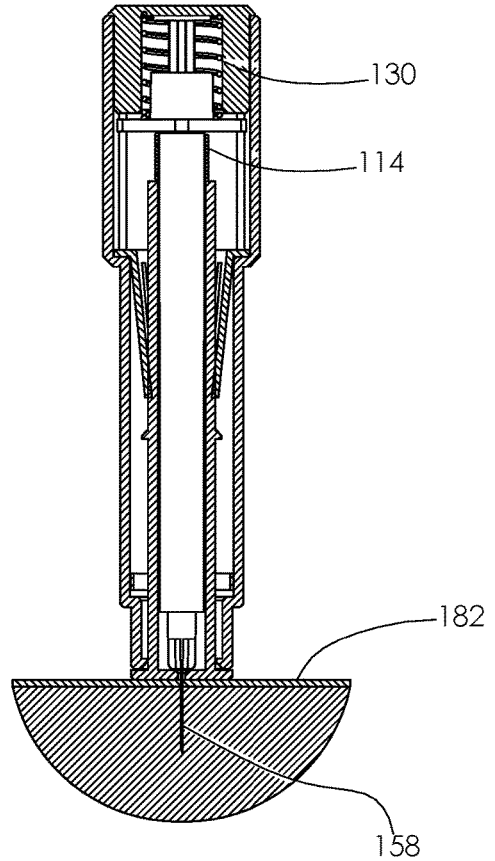
FIG. 9B is a sectional view of the medicament device and site taken along line 9B-9B seen in FIG. 9A.
Figure 11A:
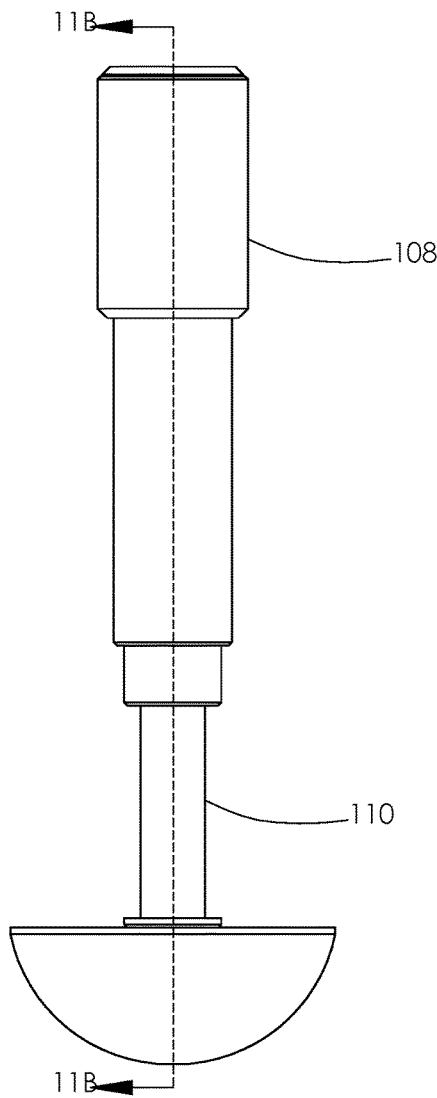
FIG. 11A is a front view of the medicament device seen in FIG. 1, wherein the device is in a fully released state after the medicament contained in the syringe has been injected into the site.
Figure 11B:
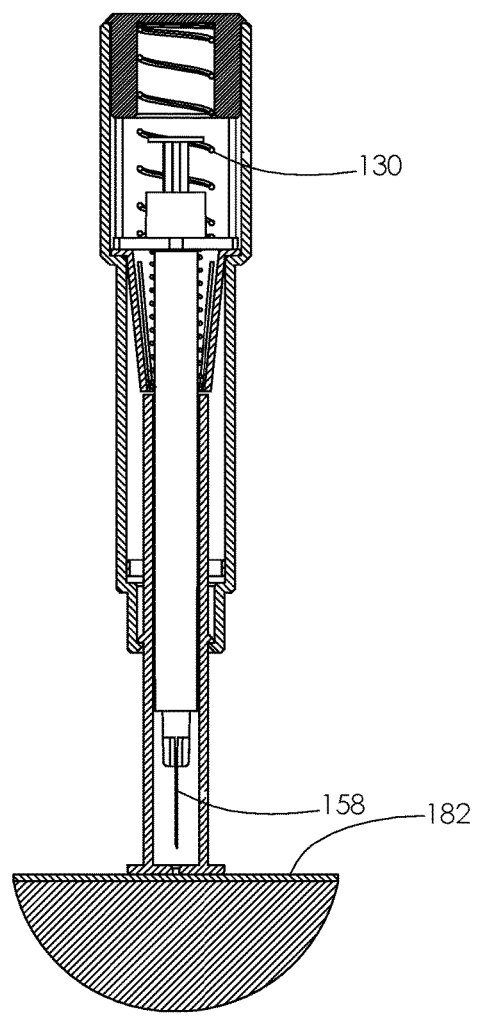
FIG. 11B is a sectional view of the medicament device and site taken along line 11B-11B seen in FIG. 11A.
Figure 12A:
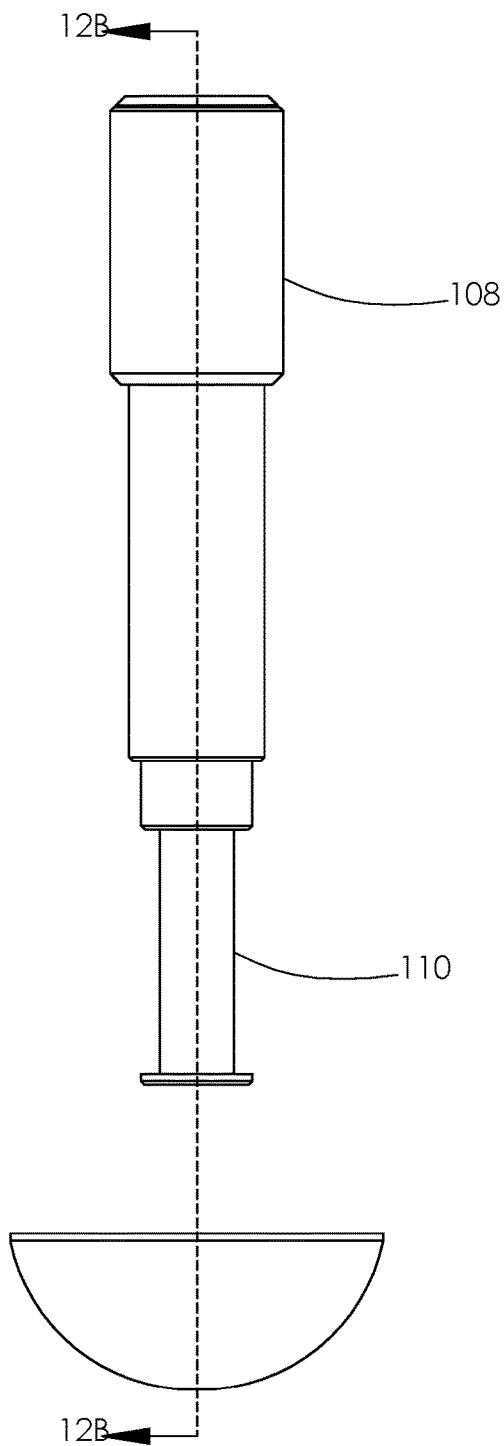
FIG. 12A is a front view of the medicament device seen in FIG. 1 disposed directly above the site after injection.
Figure 12B:
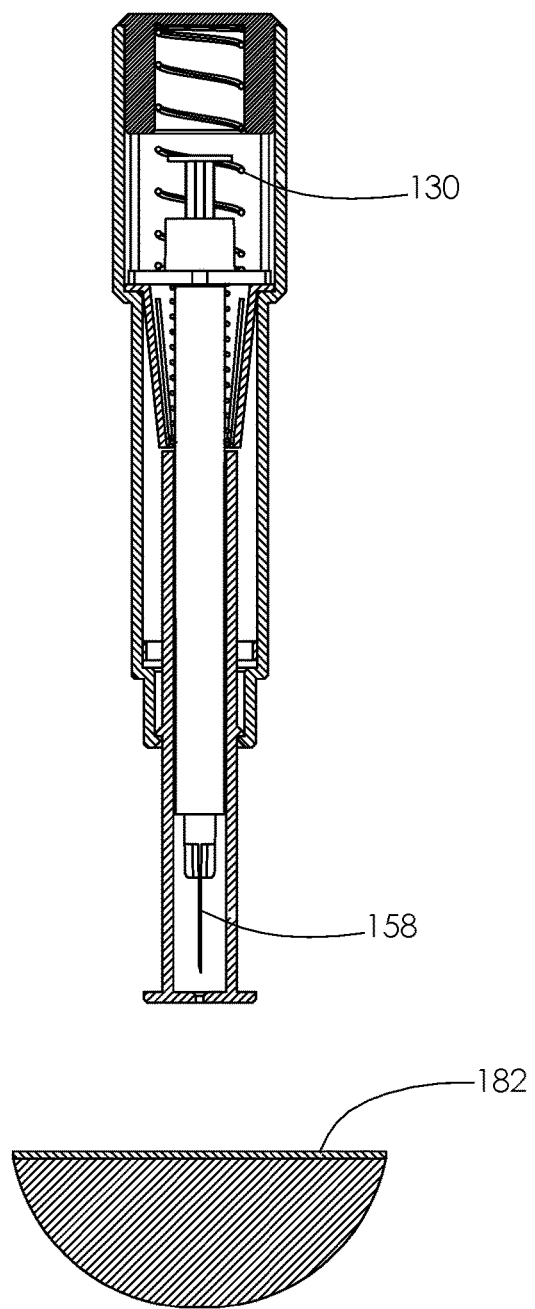
FIG. 12B is a sectional view of the medicament device and site taken along line 12B-12B seen in FIG. 12A.
Figure 13:
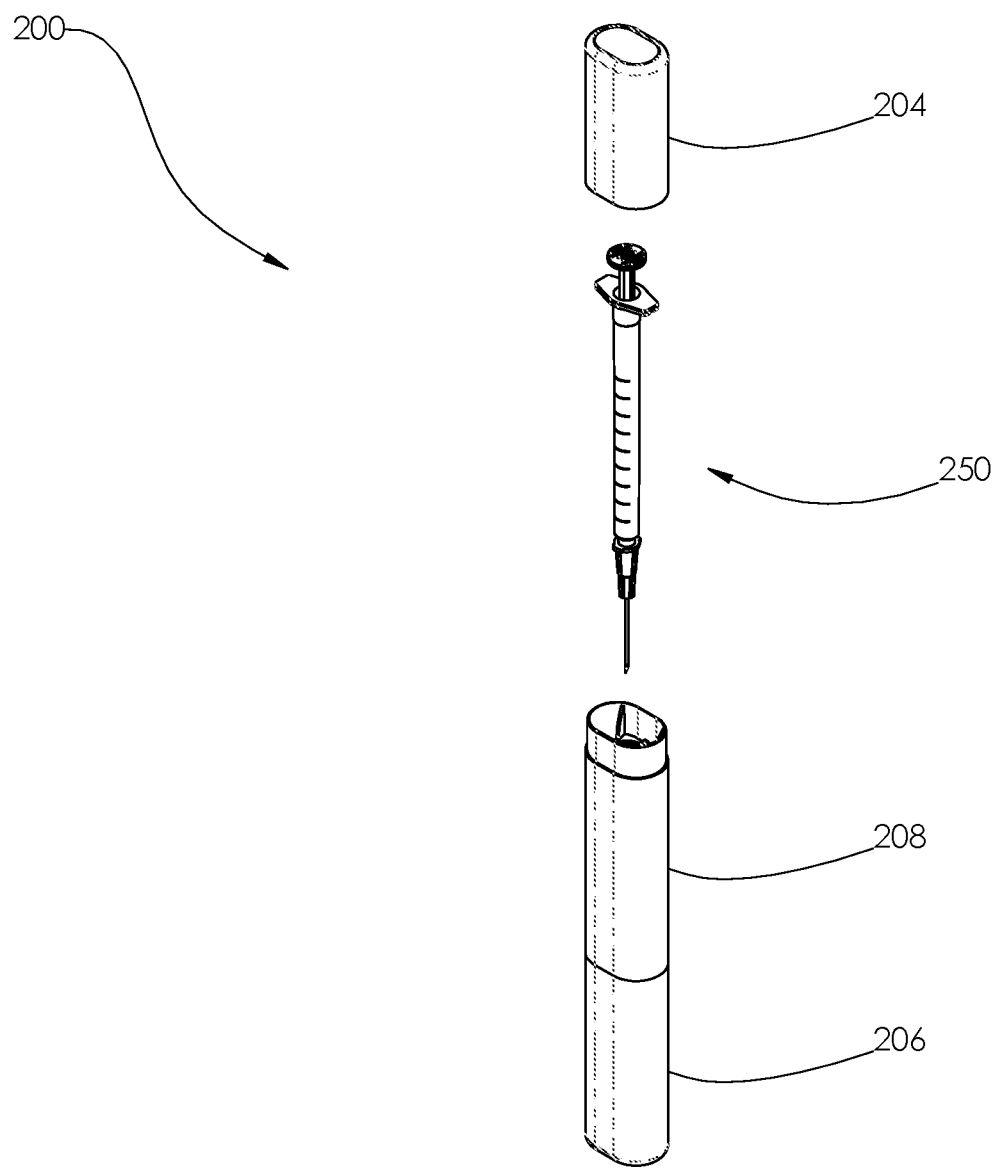
FIG. 13 illustrates a partially exploded view of another embodiment of a medicament device disclosed herein.
Figures 15A, 15B, 15C, 15D:
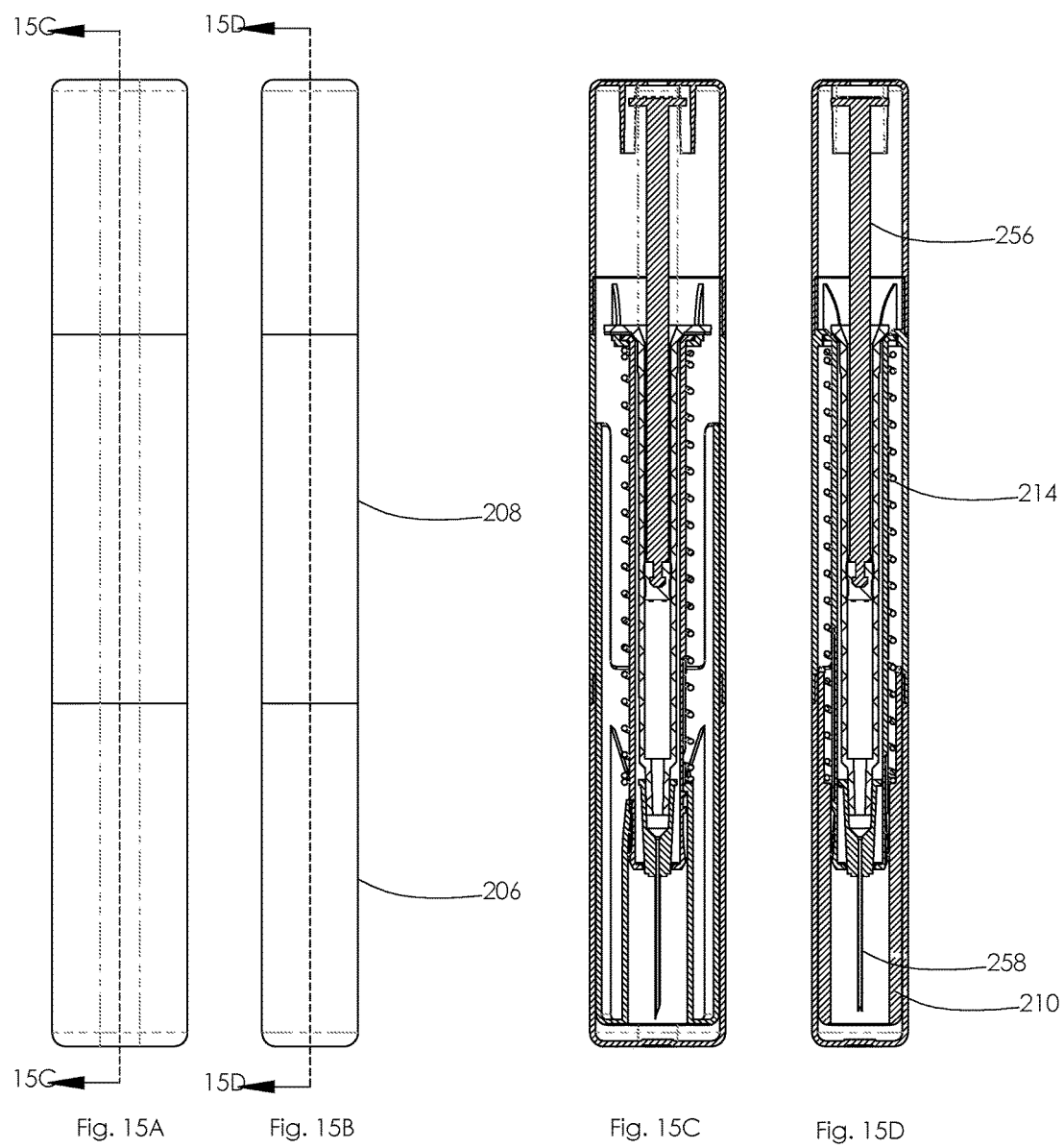
FIG. 15A is a front view of the medicament device seen in FIG. 13.
FIG. 15B is a side view of the medicament device seen in FIG. 13.
FIG. 15C is a sectional view of the medicament device taken along line 15C-15C seen in FIG. 15A.
FIG. 15D is a sectional view of the medicament device taken along line 15D-15D seen in FIG. 15B.
Figures 16A, 16B, 16C, 16D:
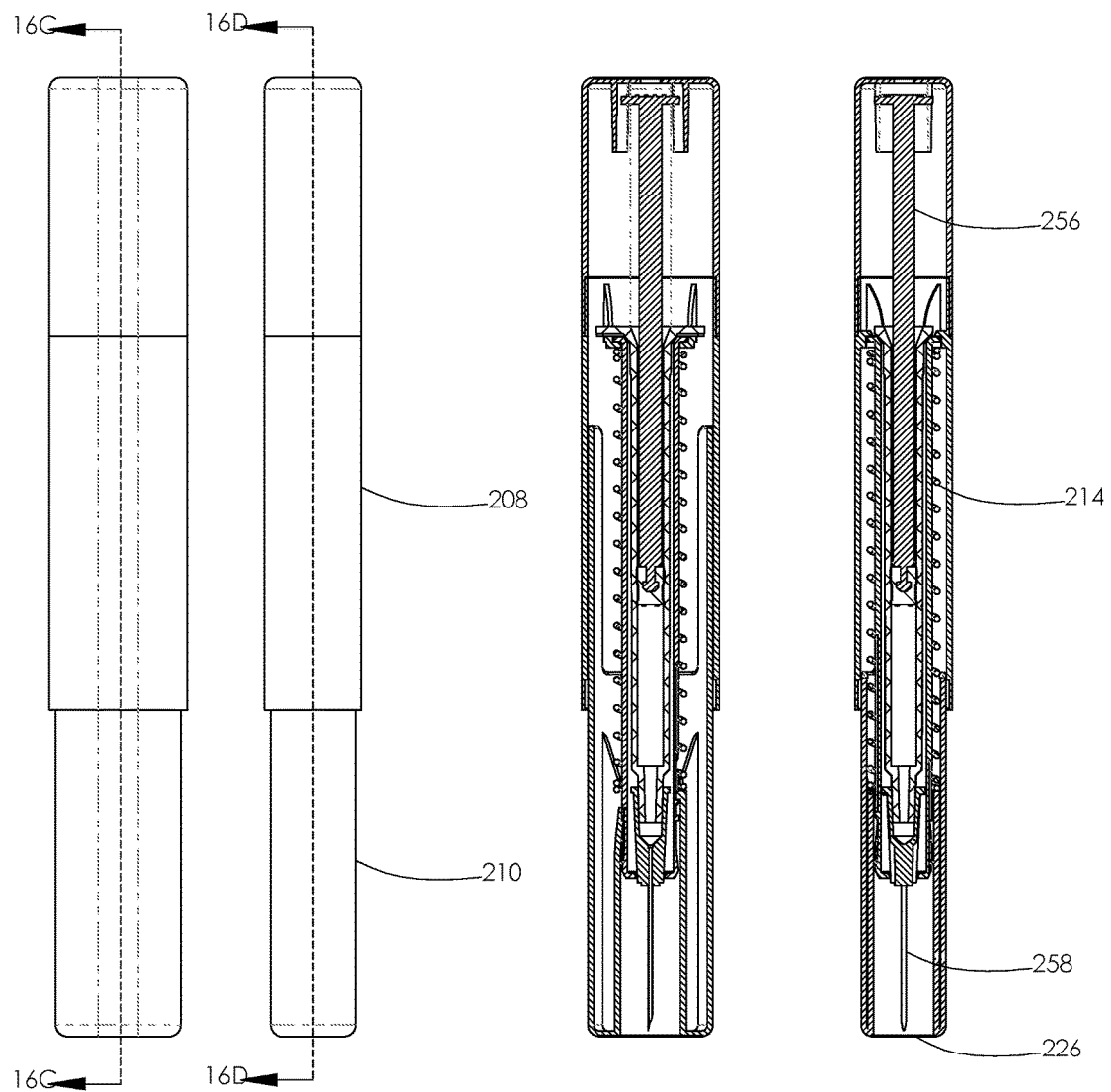
FIG. 16A is a front view of the medicament device seen in FIG. 13 with the sheath cap removed.
FIG. 16B is a side view of the medicament device seen in FIG. 13 with the sheath cap removed.
FIG. 16C is a sectional view of the medicament device taken along line 16C-16C seen in FIG. 16A.
FIG. 16D is a sectional view of the medicament device taken along line 16D-16D seen in FIG. 16B.
Figures 18A, 18B, 18C, 18D:
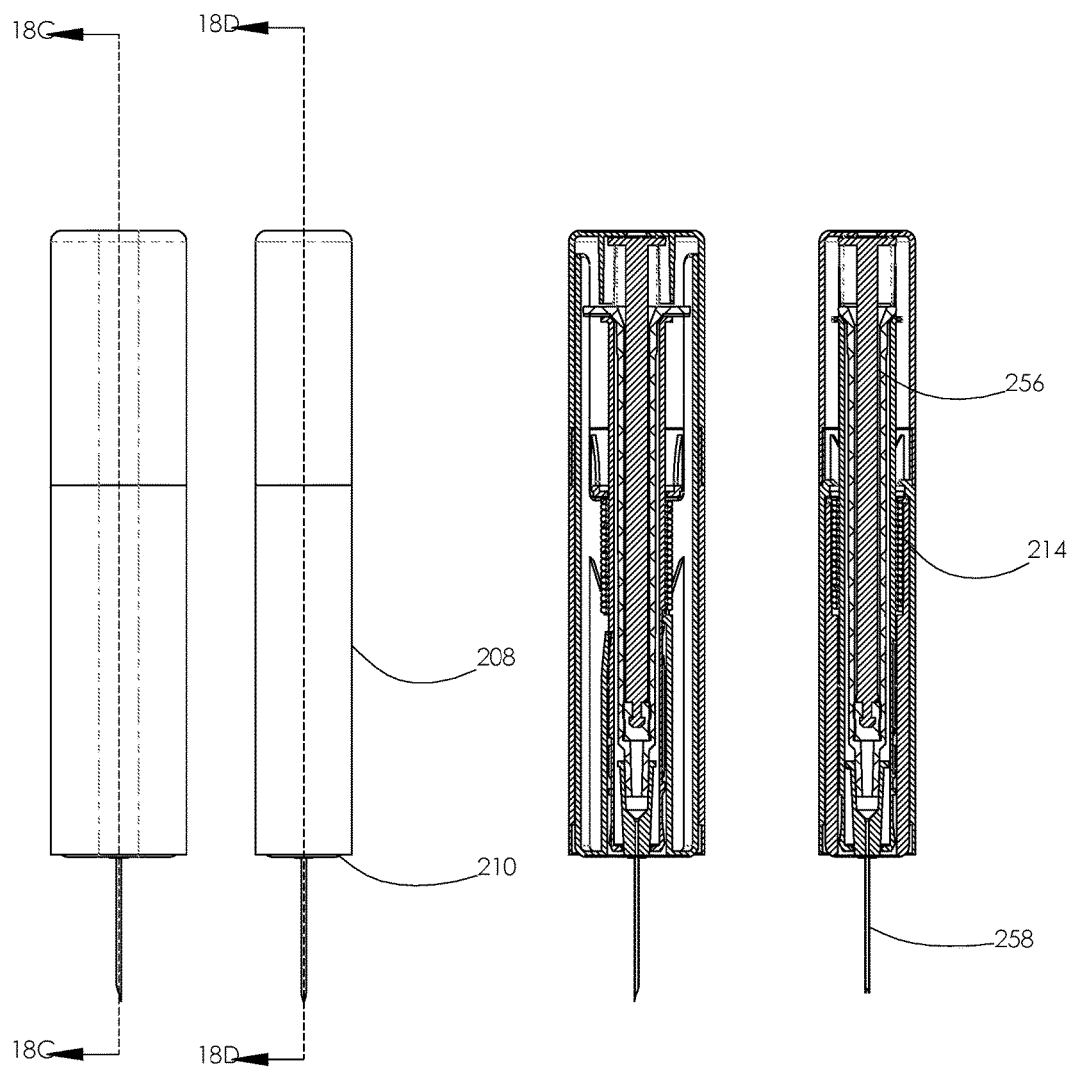
FIG. 18A is a front view of the medicament device seen in FIG. 16A with medicament in the process of being injected.
FIG. 18B is a side view of the medicament device seen in FIG. 16A with medicament in the process of being injected.
FIG. 18C is a sectional view of the medicament device taken along line 18C-18C seen in FIG. 18A.
FIG. 18D is a sectional view of the medicament device taken along line 18D-18D seen in FIG. 18B.
Figures 19A, 19B, 19C, 19D:
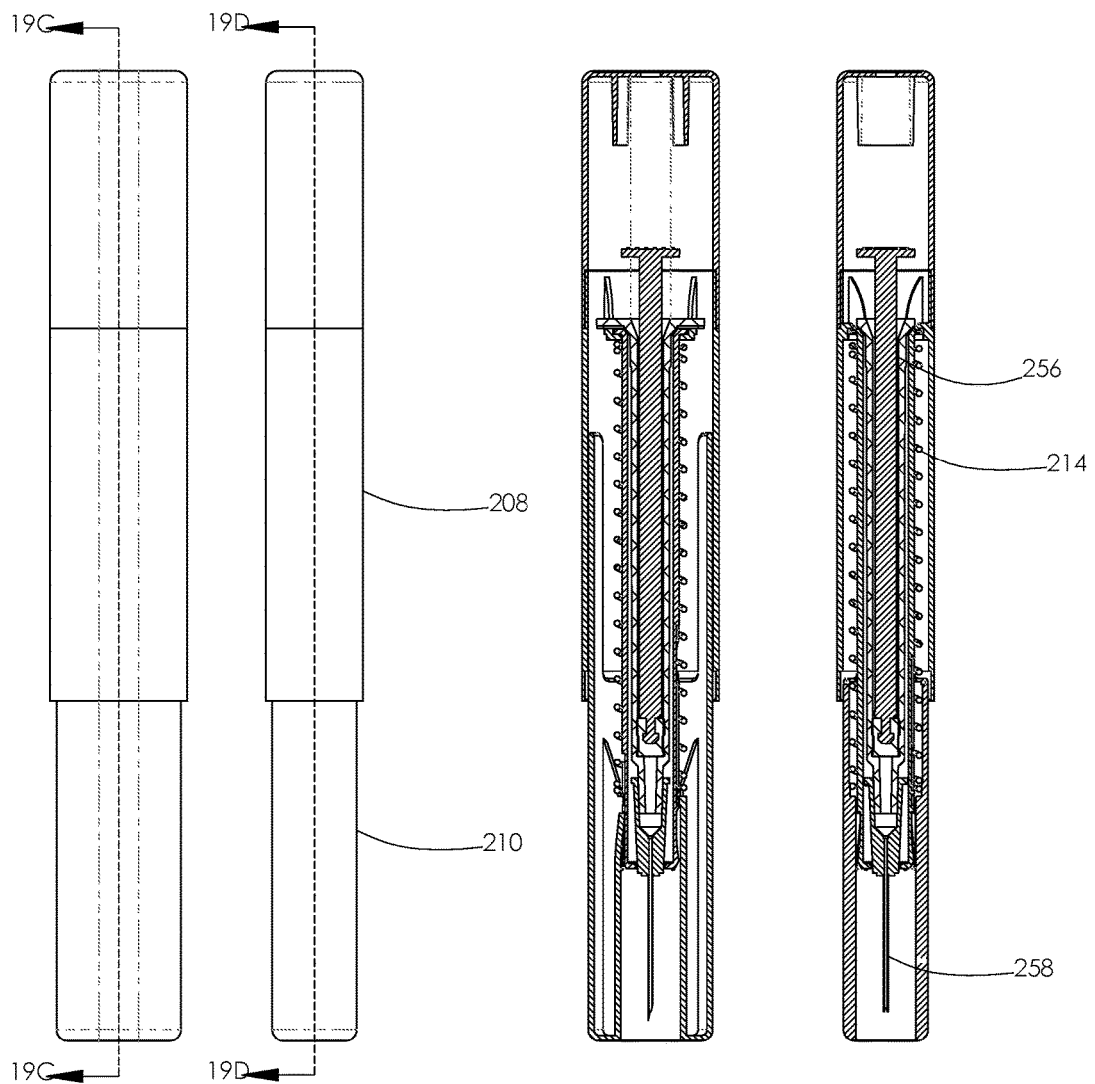
FIG. 19A is a front view of the medicament device seen in FIG. 16A, wherein the device is in a fully released state after the medicament contained in the syringe has been injected into the site.
FIG. 19B is a side view of the medicament device seen in FIG. 16A, wherein the device is in a fully released state after the medicament contained in the syringe has been injected into the site.
FIG. 19C is a sectional view of the medicament device taken along line 19C-19C seen in FIG. 19A.
FIG. 19D is a sectional view of the medicament device taken along line 19D-19D seen in FIG. 19B.
Figures 20A, 20B, 20C, 20D:
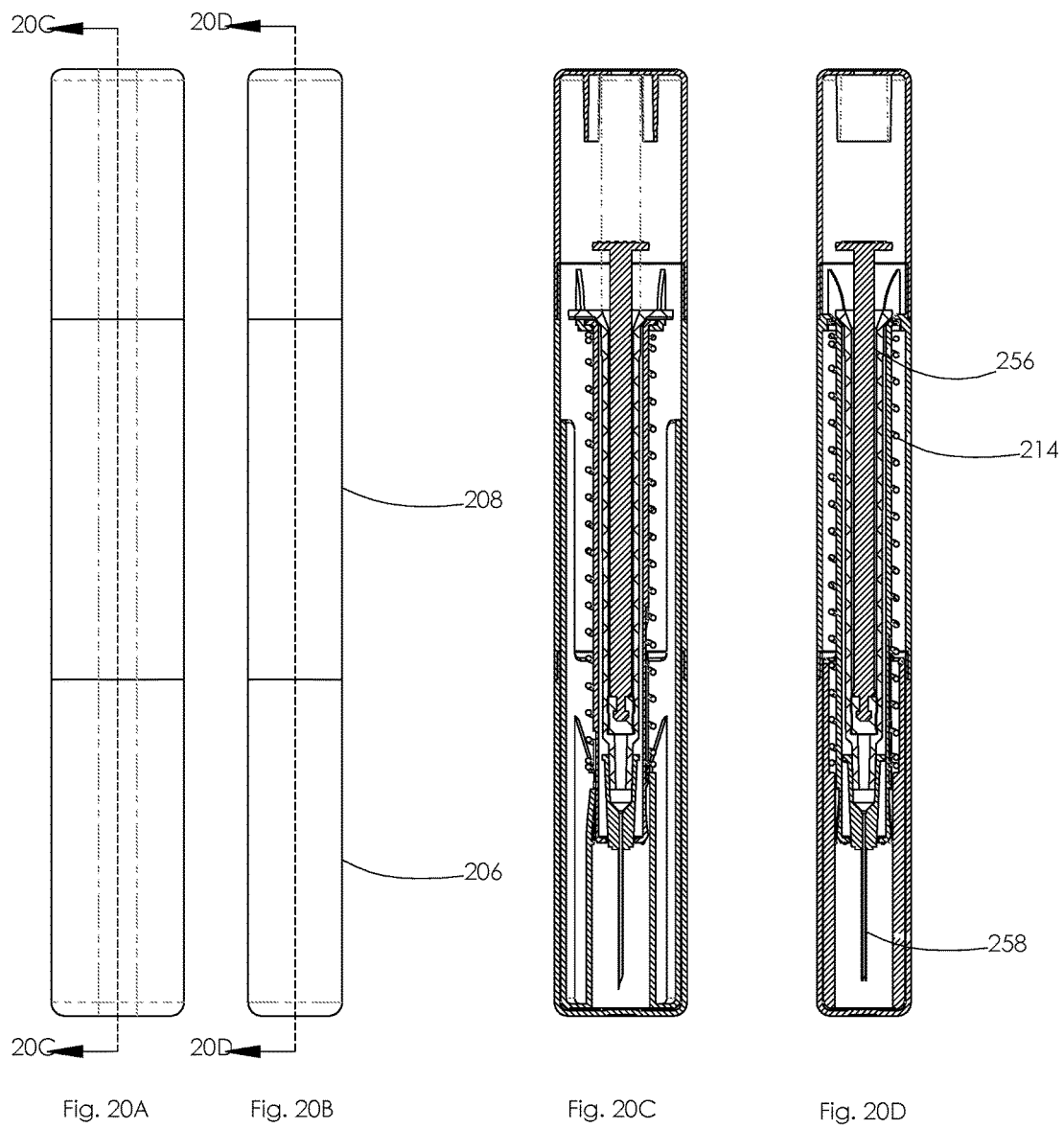
FIG. 20A is a front view of the medicament device seen in FIG. 16A, wherein the device is in a fully released state after the medicament contained in the syringe has been injected into the site and after the device has been recapped for disposal.
FIG. 20B is a side view of the medicament device seen in FIG. 16A, wherein the device is in a fully released state after the medicament contained in the syringe has been injected into the site and after the device has been recapped for disposal.
FIG. 20C is a sectional view of the medicament device taken along line 20C-20C seen in FIG. 20A.
FIG. 20D is a sectional view of the medicament device taken along line 20D-20D seen in FIG. 20B.
Figures 21A, 21B, 21C, 21D:
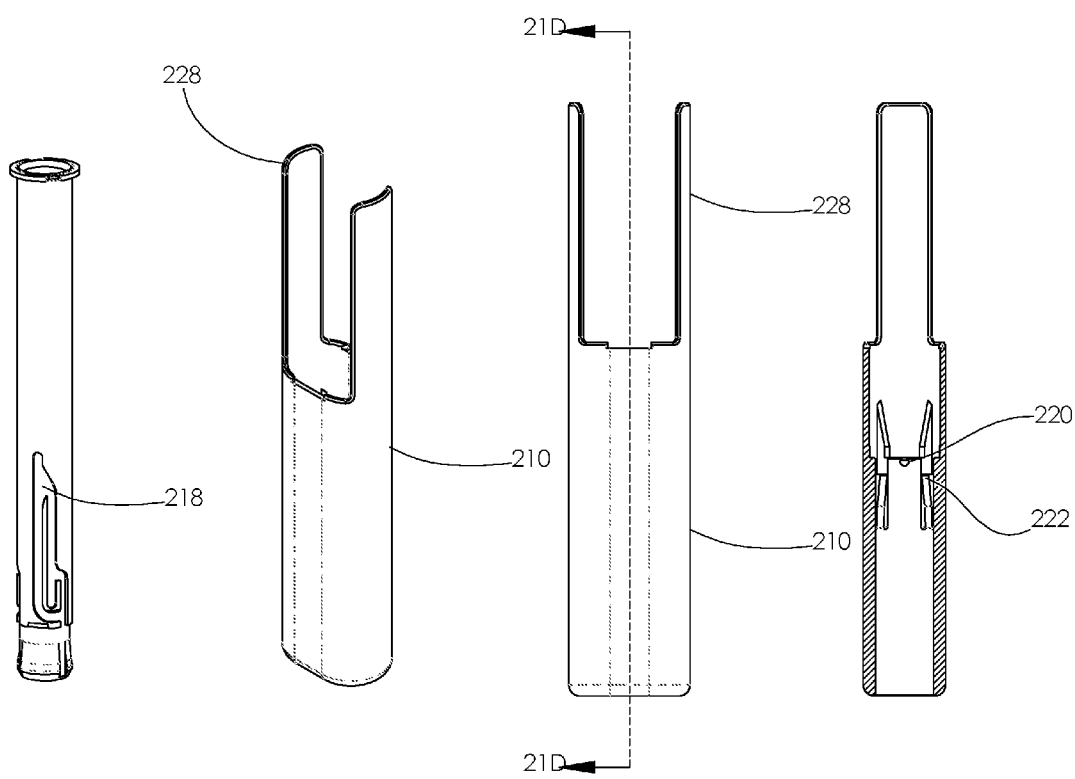
FIG. 21A is a perspective view of the sleeve of the medicament device of FIG. 13.
FIG. 21B is a perspective view of the sheath of the medicament device of FIG. 13.
FIG. 21C is a front view of the sheath seen in FIG. 21B.
FIG. 21D is a sectional view of the sheath taken along line 21D-21D seen in FIG. 21C.

FIGS. 4A-12B show the medicament device 100 in various stages of use. FIGS. 4A and 4B respectively show a front and sectional view of the device 100 fully assembled and capped by cap 106 for safe storage and transportation. FIGS. 5A and 5B respectively show a front and sectional view of the device 100 with cap 106 removed. FIGS. 6A and 6B respectively show a front and sectional view of the device 100 with cap 106 removed, wherein the sheath 110 is disposed directly above a site 180 to be injected once the needle 158 passes through skin 182. FIGS. 7A and 7B respectively show a front and sectional view of the device 100 with cap 106 removed, wherein sheath 110 is touching site 180 to be injected. FIGS. 8A and 8B respectively show a front and sectional view of the device 100 with cap 106 removed, wherein the needle 158 is deployed and passing through skin 182 and sheath spring 114 can be seen compressed. FIGS. 9A and 9B respectively show a front and sectional view of the device 100 with cap 106 removed to deliver medicament to the site 180 and produce an audible clip from the sheath lock 112 snapping past the end of the needle sheath 110. Both sheath spring 114 and plunger spring 130 can be seen compressed in FIG. 9. FIGS. 10A and 10B respectively show a front view and sectional view of the device 100 with cap removed, wherein the device 100 is in a partially released state after the medicament contained in the syringe 150 has been injected into the site 180. FIGS. 11A and 11B respectively show a front view and sectional view of the device 100 with cap removed, wherein device 100 is in a fully released state after the medicament contained in the syringe 150 has been injected into the site 180. FIGS. 12A and 12B respectively show a front view and sectional view of the device 100 with cap removed, wherein the device 100 is disposed above the site 180 after injection.

In typical operation, the cap assembly 106 is removed and the sheath 110 is placed against an intended injection site 180. The user then pushes down on the device 100. Continued pushing causes spring-loaded sheath 110 to retract into the housing 108, progressively exposing the syringe needle 158 until completely inserted into the injection site 180. As the stroke is continued beyond the full insertion of the needle 158, the proximal edge of the spring-loaded sheath 110 contacts the underside of the flanges 154 of the syringe barrel 152. Because the movement of the barrel 152 is constrained by the housing 108, the plunger 156 moves within its stationary barrel 152, expelling medicament through the needle 158. The sheath spring 114 requires less compression force than the syringe plunger spring 130, the effect being that the primary stroke lets the needle 158 pierce the skin 182 while the needle sheath 110 retracts. The secondary and culminating stroke actuates the plunger 156, effectively dispensing the bolus of medicament only when the needle 158 is fully inserted into the skin 182. In addition to feeling the device 100 bottom out, the user feels and hears a click confirming stroke completion. The shot having been administered, the user stops pushing down on the device 100 whereby the needle 158 is withdrawn as the spring-loaded sheath 110 extends and locks with a second click upon full extension preventing further use of the device 110. Thus, the sheath lock 116 retains the needle sheath 110 in an extended position that covers the needle 158 of the syringe 150 after injection is complete.

FIGS. 13-21 illustrate another embodiment of a device 200 for administering a medicament such as by an injection using a conventional pre-filled syringe 250. Such a syringe 250 may comprise a barrel 252, plunger 256 that slides within barrel 252, and needle 258. The barrel 252 typically has flanges 254 at one end that aid in pushing the plunger 256 through the barrel 252 containing medicament (not shown) to be administered by a user or patient.

Medicament device 200 preferably comprises a body assembly 202, a sheath cap 206 at end of the assembly 202, and a housing cap 204 with its optional label 224 at the other end of the assembly 202.

Body assembly 202 may be comprised of a housing 208 containing sheath 210 with its optional sheath seal 226, locking mechanism 212, and sheath spring 214. The locking mechanism 212 preferably comprises a sleeve 216 having sleeve tracks 218 configured to receive one or more sheath pins 220 protruding from the interior of sheath 210, as well as sheath snaps 222 disposed about the interior of sheath 210 and protruding therefrom, as illustrated in FIGS. 21A-21D. Sheath seal 226 may serve to seal the chamber of syringe 250 until pierced by the needle 258.

As best seen in FIG. 14B, housing 208 is generally tubular in shape with a top and an opposing bottom. The top of housing 208 is configured to receive and frictionally engage a conventional syringe 250 placed into the housing 208 from the top. The top of housing 208 is also configured to receive the sleeve 216 having an opening at one end configured to receive syringe 250. The bottom of the housing 208 is configured to receive the sheath 210 wherein the sheath 210 may freely slide within the housing 208.

The overall length of the housing 208 is about the same length of the barrel 252 of conventional syringe 250. Similarly, the overall length of sheath 210 with its sheath fingers 228 is also about the same length of the barrel 252.

When assembled, the entire syringe 250 with its needle 258 is encased within the device 200. Sheath cap 206 and sheath 210 surround the needle 258 when the device 200 is not in use. Housing cap 204 seals the top of the housing 208.

FIGS. 15A-20D show the medicament device 200 in various stages of use. FIGS. 15A-15D show the device 200 fully assembled and capped by cap 206 for safe storage and transportation. FIGS. 16A-16D show the device 200 with cap 206 removed. FIGS. 17A-17D show the device 200 in a stage whereby the needle 258 is deployed to deliver medicament. FIGS. 18A-18D show the device 200 with spring 214 in a compressed state wherein medicament has been delivered or is being delivered. FIGS. 19A-19D show the device 200 in a fully released state after the medicament has been delivered. FIGS. 20A-20D show the device 200 in a fully released and locked state with the device being recapped for disposal.

In typical operation, the cap assembly 206 is removed and the sheath 210 is then placed against an intended injection site. The user then pushes down on the device 200. Continued pushing causes spring-loaded sheath 210 to retract into the housing 208, progressively exposing the syringe needle 258 until it is completely inserted into the injection site, fully compressing sheath 210 wherein sheath fingers 228 slide within housing body 208. Concurrently, sheath pins 220 found on the internal surface of sliding sheath 210 track in sleeve tracks 218, effectively guiding and rotating the sleeve 216 concentrically as the sheath 210 draws in and into bifurcated sleeve tracks 218.

When sheath 210 is fully compressed into body 208, sheath fingers 228 contact and spread sheath snaps 222 to permit the plunger 256 to slide within barrel 252 and thereby expel medicament through syringe needle 258.

The shot having been administered, the device 200 is then removed from the injection site, withdrawing syringe needle 258 and allowing spring-loaded sheath 210 to re-extend from the body 208 due to the biasing force of sheath spring 214. Sheath pins 220 track in the straight and slightly longer bifurcation found in the now-rotated sleeve tracks 218. At full extension, sheath 210 bottoms out at a position slightly more extended than its initial position, thus allowing sheath snaps 222 to engage and lock out sheath 210 for the purpose of protecting syringe needle 258, thereby preventing further use of the device 200.

The disclosed inventions advantageously may use a conventional syringe pre-loaded by the user for pre-filled, portable injections (e.g., insulin, epinephrine). The device 100, 200 may be produced in varying lengths and sizes to accommodate different syringe sizes (e.g., 0.3 mL, 1 mL, 3 mL). The device 100, 200 may also be produced in a length that precludes over-filling the syringe beyond a set dosage, and thus avoid a potential overdose.

The disclosed inventions may also function with any prescribed quantity of medicament equal to or less than full capacity. For example, the device 100, 200 may be adjusted to dispense varying doses of medicament by means of a coarsely threaded cap, which may be adjusted to vary the travel length of syringe plunger, with indices showing the relative amount of medicament to be dispensed.

The housing of the device 100, 200 may also include a window to provide a direct view of the medication. Such a window may be circumscribed with a color that, when matched with the medicament color as viewed through said window, indicates the medicament has expired. In such a situation, the syringe may advantageously be changed out for a new syringe with non-expired medicament.

The sheath may be marked with color or graphics to let the user know the syringe needle is fully inserted (triggering medicament injection). In the alternative, a battery-powered light emitting diode or the like may illuminate to indicate the syringe needle is fully inserted.

The housing may be made of a transparent material that reveals the inner functioning of the device, including revealing the amount of medicament in syringe. The housing may also incorporate instructional graphics.

The device 100, 200 may include a peel-off-cover antiseptic pad for the purpose of cleaning the injection site. Such a pad may be adhered to the housing cap, for example.

The housing cap may permanently lock when inserted into housing, sealing in the syringe to assure single-use only. In the alternative, the housing cap may be removable to change out the syringe as desired so the device may be further used. If desired to limit reuse of device 100, 200, then the housing cap may be removable by means of a special tool.

The device 100, 200 may be made of disposable, single-use materials, or alternatively, made of reusable materials that could withstand repeated sterilization. Regardless of the materials used, the device 100, 200 may incorporate a peel tab or breakaway part that renders the device non-functional after a single use, insuring single-use only.

The medical device 100, 200 may also include a split thrust washer located between the syringe flanges and the housing cap that deforms when squeezed to provide a tactile and audible click when the plunger is fully depressed, letting the user know that the stroke is complete, all medicament is dispensed, and the shot has been successfully administered.

The device 100, 200 may integrate a voice-chip to provide audible instructions and status such as when a medicament has expired or is nearing the expiration date. Similarly, the device 100, 200 may integrate a chemical or mechanical timer to indicate when a determined number of days have passed since syringe filling, indicating expiration of contents. Such a timer may be activated when the housing cap is closed to begin the countdown to medicament expiration.

The device 100, 200 may include a shrink-wrap thermoplastic with graphics wherein the wrap is applied to seal and retain the protective cap and then peeled away for use. Similarly, the housing body may be sheathed in shrink-wrap thermoplastic with graphics showing instructional information, expiration date, custom branding, or the like.

The device 100, 200 may include a flat surface on an otherwise cylindrical body to keep the device from rolling. Such a flat surface may be used to print indicia via a felt-tip marker or the like.

The device 100, 200 may include a rotating collar on an otherwise cylindrical body that is positioned by the assembler or user to show the loaded medicament dose. The rotating collar may then be locked into place by virtue of device assembly.

The device 100, 200 may include a metal sleeve within housing, which when pre-chilled with ice or refrigeration, provides cooling for heat-sensitive medicament. In the alternative or in addition thereto, the device 100, 200 may be shaped to fit into a refrigerated chiller to pre-cool heat-sensitive medicament during transportation.

The housing may be configured to contain a plurality of syringes in the event that administration of initial injection is inadequate to treat the present condition (e.g., epinephrine administration for anaphylaxis typically calls for a second dose if symptoms do not abate in a timely manner) or for convenience of having more than one injection at hand (e.g., fertility injections are typically timed hourly).

The device 100, 200 may also be used for oral medication dispensation, concealing a standard syringe and its association with needles.

It should now be apparent that the disclosed inventions have many advantages over conventional devices. Auto-injectors, upon trigger-release, automatically inject needle and medicament, presumably into an intended injected site. Unlike auto-injectors, the disclosed inventions do not automatically insert the needle, an advantage in avoiding accidental actuation that happens with auto-injectors.

Moreover, the disclosed inventions rely on manual action to insert the needle at the injection site, like a standard syringe, making needle sticks less likely than when using and auto-injector, which fires its needle upon contact with any surface, including hands, thumbs, and fingers. The disclosed inventions also inject medicament only after the needle is fully inserted, unlike auto-injectors, which inject medicament immediately upon trigger release. Safety issues, such as a child accidentally firing an adult-dosage auto-injector and thereby receiving twice the recommended amount of medicament for their size, are thus avoided. Also avoided is the dispensing of medicament along the needle tract during insertion, where medicament may not get to its intended target area as may occur with conventional auto-injectors.

The disclosed inventions also facilitate hypodermic injection using an evolved, standard ubiquitous syringe rather than a proprietary or custom syringe that may fail. Moreover, the disclosed inventions may be filled to a prescribed dose of medicament rather than "one-dose-fits-all" as found with auto-injectors and factory-filled syringes. Such pre-loading of medicament may conveniently be done in a domestic setting such as the user's home, in a clinical setting such as a doctor's office, or in an institutional setting such as a school. Indeed, as the contained syringe is pre-filled to a prescribed dosage, the disclosed inventions are ready for use and may be rapidly deployed and used in emergency or military situations.

The sheath cap of the disclosed inventions also acts as both protector and safety cover against accidental activation. Moreover, after use, the locking mechanism of the device 100, 200 protects the needle from being extended from the sheath when the sheath cap is not present, resulting in another advantageous and novel safety feature.

The disclosed inventions are also simpler and safer than administering shots with a standard syringe aspirating from a standard vial. Fortunately, the use of the disclosed inventions is not dissimilar to the customary administering of a typical shot. Such action is in contrast to the violent firing of a needle into skin as is done with the auto-injector. Moreover, because the contained syringe is pre-filled to a prescribed dosage, an unskilled user may quickly and safely administer a shot.

Finally, the disclosed injectors have only two actions to administer a shot: removing the housing cap and pushing down the device on an intended injection site. Conventional auto-injectors require removal from a carrier tube, removal of a locking key, and then pushing onto the intended injection site.

While certain embodiments have been described, the embodiments have been presented by way of example only and are not intended to limit the scope of the inventions. Indeed, the semi-automatic injector disclosed herein may be embodied in a variety of other forms. Furthermore, various omissions, substitutions, and changes in the form of the disclosed elements may be made without departing from the spirit of the inventions.

The invention claimed is:

1. A device for administering medicament using a conventional syringe, the device comprising:

a body assembly configured to receive a conventional syringe, the body assembly having a top and an opposing bottom; and a housing cap at the top of the body assembly;

wherein the body assembly comprises a housing, a sheath slideably contained within the housing, a locking mechanism, and a sheath spring, wherein the locking mechanism comprises a sleeve, sleeve tracks, and one or more sheath pins, wherein the sleeve is slideably disposed within the housing at an end opposite the sheath, wherein the one or more sheath pins protrude from an interior of the sheath, and wherein the sleeve tracks are cut within the sleeve and configured to engage the one or more sheath pins.

2. The medicament device of claim 1, wherein the locking mechanism further comprises sheath snaps extending from the interior of the sheath, and wherein the sheath has sheath fingers extending from one end of the sheath for engaging the sheath snaps.

3. The medicament device of claim 1, wherein the housing is substantially the same length as a barrel of the conventional syringe.

4. The medicament device of claim 1, wherein the sheath is substantially the same length as a barrel of the conventional syringe.

5. A device for administering medicament using a conventional syringe, the device comprising:

a body assembly configured to receive a conventional syringe, the body assembly having a top and an opposing bottom; and a housing cap at the top of the body assembly;

wherein the body assembly comprises a housing, a sheath slideably contained within the housing, a locking mechanism, and a sheath spring, wherein the locking mechanism comprises a sleeve, one or more sheath pins, and sleeve tracks, wherein the sleeve is slideably disposed within the housing at an end opposite the sheath, wherein the one or more sheath pins protrude from an interior of the sheath, wherein the sleeve tracks are cut within the sleeve and configured to engage the one or more sheath pins, and wherein the sleeve tracks are bifurcated to lock the sheath in place around a needle of the conventional syringe after use of the device to administer medicament.

6. The medicament device of claim 5, wherein the locking mechanism further comprises sheath snaps extending from the interior of the sheath, and wherein the sheath has sheath fingers extending from one end of the sheath for engaging the sheath snaps.

7. The medicament device of claim 5, wherein the housing is substantially the same length as a barrel of the conventional syringe.

8. The medicament device of claim 5, wherein the sheath is substantially the same length as a barrel of the conventional syringe.

* * * * *